(12) United States Patent
Titmas

(10) Patent No.: US 6,383,736 B1
(45) Date of Patent: *May 7, 2002

(54) PERSONAL DRUG USE INDICATOR

(76) Inventor: Ted Titmas, 26012 Marguerite Pkwy. #H204, Mission Viejo, CA (US) 92692

( * ) Notice: Subject to any disclaimer, the term of this patent is extended or adjusted under 35 U.S.C. 154(b) by 0 days.

This patent is subject to a terminal disclaimer.

(21) Appl. No.: 09/515,381

(22) Filed: Feb. 29, 2000

(51) Int. Cl.[7] .............................. C12Q 1/00; C12M 1/00; G01N 33/53

(52) U.S. Cl. ..................... 435/4; 435/283.1; 435/975

(58) Field of Search ...................... 435/4, 283.1, 975

(56) References Cited

U.S. PATENT DOCUMENTS 5,563,073 A  * 10/1996  Titmas ..................... 436/132

* cited by examiner

Primary Examiner—Louise N. Leary
(74) Attorney, Agent, or Firm—Oppenheimer Wolff & Donnelly LLP

(57) ABSTRACT

A personal drug testing kit utilizing drug-sensitive pads which are stored in a package that permits the storage of the drug-sensitive pads within its interior without exposing the drug-sensitive pads to ultraviolet light, moisture or air. The kit comprises at least one pad being chemically sensitive to a predetermined drug. The drug-sensitive pads are stored in a package that is preferably formed from aluminum foil and paper and that is free from air. The drug testing kit may test for the presence of one or more of the following drugs of abuse: marijuana, cocaine, opiates, PCP, amphetamines, methamphetamines, and barbituates.

31 Claims, 1 Drawing Sheet

PERSONAL DRUG USE INDICATOR

FIELD OF THE INVENTION

The present invention relates in general to personal drug testing kits and more particularly to the packaging for storing the drug-sensitive pads of a personal drug testing kit and to the method for testing the presence of a certain drug or drugs that have possibly been taken by the user. The invention is also applicable to the storage of the drug-sensitive pads which must be protected from any contact with ultraviolet light, moisture, or air.

BACKGROUND OF THE INVENTION

It is often necessary for a parent or an employer to be able to determine whether their son, daughter, or employee have ingested any of a number of illegal and harmful drugs, such as marijuana, cocaine, opiates, PCP, amphetamines, methamphetamines, and barbituates. While there are numerous known means for detecting these drugs, these known means often include the taking of a blood or urine sample. It is not practical, however, for a parent or an employer to take such a blood or urine sample to quickly determine whether their son, daughter, or employee has ingested such drugs. Further, the use of urine samples presents numerous opportunities for manipulation, as has been well-documented. For these reasons, at this time, it is nearly impossible for a parent or employer who suspects that their son, daughter, or employee is under the influence of any of these drugs to test their son, daughter, or employee to accurately determine whether they are in fact under the influence of any of these substances.

Accordingly, there is a need for a method and testing kit that can be used by a parent or an employer to test a person for the presence of certain drugs, such as marijuana, cocaine, opiates, PCP, amphetamines, methamphetamines, and barbituates. Such a testing kit should be capable of providing immediate, accurate, and reproducible results without the taking of the user's blood or urine. The testing kit should be portable, so that it may be discreetly carried in a wallet, pocket or purse and used at a variety of locations. The testing kit also should be inexpensive so that parents and employers will be apt to purchase the kit. The testing kit should also be able to detect more than one drug, as the person may have ingested any one of a number of different substances. The kit should also be self-contained, that is, all the necessary items, including instructions and any charts or graphs, should be included within or on the packaging. The test kit should also be easy to administer—easy enough so that any one can use the test kit without any specialized training.

A testing kit that is able to detect these drugs by testing the user's saliva may be capable of meeting these needs. For example, it is known that a person's saliva contains some of the same materials that may also be present in the person's blood. One example of the testing of a person's saliva is the determination of a person's blood alcohol level. A person's saliva contains the same concentration of alcohol as in that person's blood. Test kits have been developed for detecting the level of a person's blood alcohol in that person's saliva. These test kits utilize alcohol-sensitive pads that are formed from paper saturated with alcohol oxidase enzyme, alcohol peroxidase enzyme, dyes and a buffer. When these alcohol-sensitive pads are saturated with a person's saliva, they will change color according to the level of alcohol in that saliva. Such a personal blood alcohol testing kit is disclosed in U.S. Pat. No. 5,563,073.

Accordingly, there exists a need for a personal testing kit to detect the presence of certain drugs by testing the person's saliva.

SUMMARY OF THE INVENTION

In accordance with the present invention, a personal drug testing kit that is capable of detecting the presence of one or more drugs that have been ingested by the user is provided. The test kit determines whether certain drugs are present by analyzing the person's saliva, rather than their blood or urine.

The test kit is comprised of the packaging and the pad or pads that are stored within the packaging. The pads are chemically sensitive to certain predetermined drugs and are preferably impregnated with at least one enzyme that is sensitive to the particular drug that it is searching for, at least one dye, and at least one buffer. Each pad changes color when it is contacted with the user's saliva, but only if the user's saliva contains the particular drug for which the pad is intended to test. This change in color indicates that the person's saliva contains this particular drug, and thus the test will reveal by this change in color that the person has ingested the drug that is being tested.

Each drug-sensitive pad comprises a piece of paper saturated with one or more enzymes that are sensitive to each drug that is being tested. The paper is also saturated with dyes and a buffer. The drug-sensitive pads are preferably cut into small pieces less than one-half square inch in size. The drug-sensitive pads are attached to the end of a stick so that the user may place the drug-sensitive pad within his mouth to saturate the pad with saliva or may dip the drug-sensitive pad into saliva that has been collected in a cup. If more than one drug is being tested for, then a separate drug-sensitive pad that is specific to each drug being tested for may be mounted to the same stick so that all drugs may be tested for with one application of saliva to the plurality of pads mounted onto the stick.

The drug-sensitive pads are stored in a package. The package includes a first side wall comprised of a plurality of layers coupled together with at least one of the layers being formed from aluminum foil and a second side wall also comprised of a plurality of layers coupled together with at least one of the layers being formed from aluminum foil. The aluminum foil of the first and second side walls of the package may be formed from high-grade surgical aluminum foil. Similarly, the aluminum foil may be coated with a polymer. In either case, the package is formed by coupling together the outer edge of the first side wall with the outer edge of the second side wall to form an interior for storing at least one drug-sensitive pad. The package is intended to protect the drug-sensitive pads from ultraviolet light, moisture, and air.

The instructions for use and the identity of the drug being tested by each of the pads (if more than one drug-sensitive pad is being used to detect more than one drug) may be printed on the outside surface of one of the side walls of the packaging. Thus, by printing the instructions for use on the exterior of the package, a self-contained personal drug testing kit is provided.

The user performs the personal drug test after abstaining from eating or drinking for at least fifteen minutes prior to taking the test. The test is administered by saturating the drug-sensitive pad or pads at the end of the stick with the user's saliva. Once the pad or pads are completely saturated, the user waits approximately two minutes for the drug-sensitive pad or pads to change color. If any of the pads changes color, this indicates the presence of the drug for which that particular pad is testing. If there is no change in color, then that drug is not present. Thus, an easy-to-administer test is provided that is accurate and reproducible and does not require the taking of blood or urine.

Other objects, features and advantages of the invention will become apparent from a consideration of the following detailed description and from the accompanying drawings.

DETAILED DESCRIPTION OF THE PREFERRED EMBODIMENTS

Figure 1:
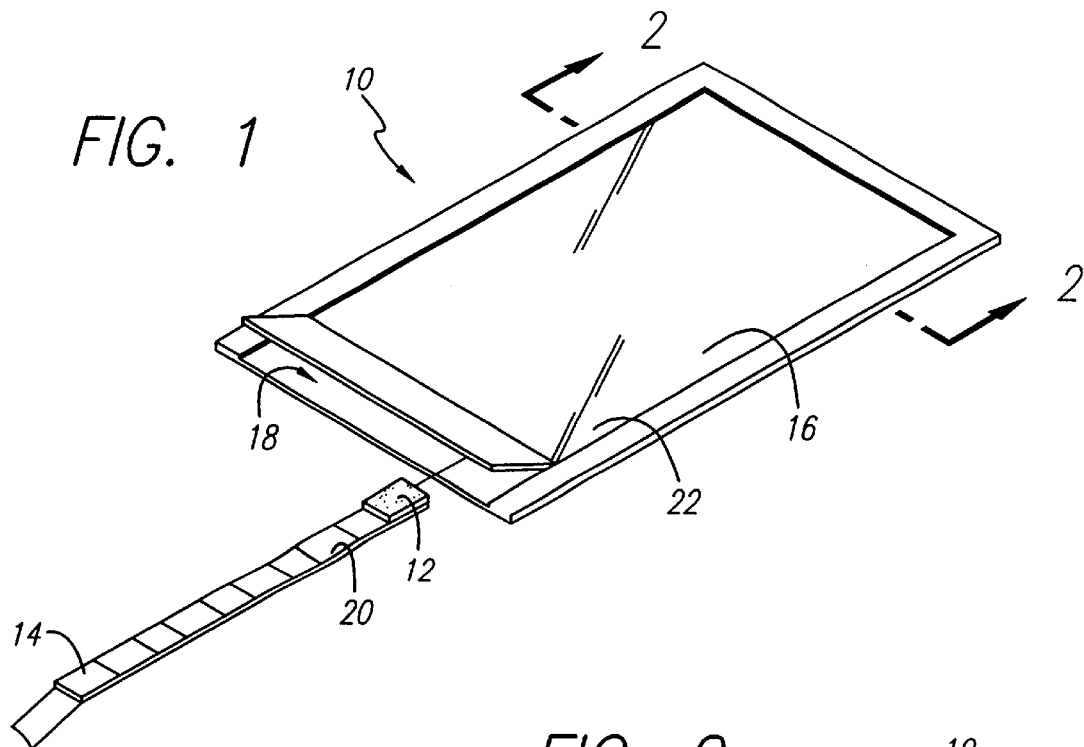
FIG. 1 is a top plan view of the package for storing the drug-sensitive pads of a personal drug testing kit showing a plurality of the drug-sensitive pads and sticks with which one embodiment of the present invention can be used.

The present invention is embodied in a personal drug testing kit for testing the presence of any one of a number of drugs in a user and includes the drug-sensitive pads and the packaging for storing the drug-sensitive pads.

In the particular embodiment shown in the drawings and herein described, the personal drug testing kit 10 (see FIGS. 1 and 2) comprises at least one drug-sensitive pad 12 that is attached to a stick 14. The sticks 14 and pads 12 are stored within a package 16. The drug-sensitive pads 12 may include one or more enzymes. These enzymes are sensitive to ultraviolet light, moisture, and air and will lose their activity if exposed to these elements for any substantial amount of time. Accordingly, these pads need to be stored in a package which prevents their exposure to these elements.

Each drug sensitive pad 12 is designed so that, when exposed to a person's saliva, the pads 12 are capable of detecting the presence of a predetermined drug. If the drug that the pad is designed to detect is in fact detected, buffers and dyes, that are also present on the drug-sensitive pad 12, are activated so that they will cause a change in color of the pad 12. The user can then examine the change in color and determine which drugs, if any, have been ingested.

Figure 2:
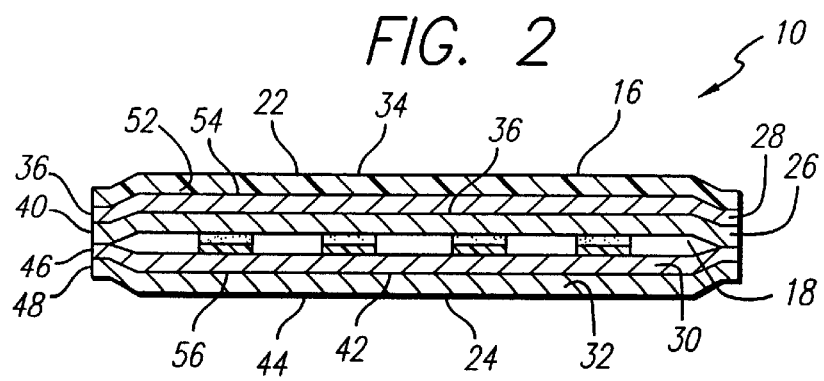
FIG. 2 is a side cross-sectional view taken along the line 2—2 in FIG. 1 containing four sticks with pads.

At least one drug-sensitive pad 12 is provided within the interior 18 of the package 16. (FIGS. 1 and 2). The drug-sensitive pads 12 are preferably formed from a piece of paper saturated with one or more enzymes, one or more dyes, and one or more buffers. Each drug-sensitive pad is designed to be sensitive to a particular, specific drug. In other words, one pad may be sensitive to marijuana. Thus, this pad would be saturated with the enzyme or enzymes that are sensitive to the marker for marijuana that will be present in a person's saliva when the person has ingested or smoked marijuana and the marijuana is still present in the person's bloodstream. In addition, this pad 12 should further include one or more dyes and buffers which will cause a change in color when the marijuana-sensitive enzyme or enzymes are activated by the marijuana marker in the saliva. Any enzyme, dye, and buffer, or combination thereof, may be selected, so long as the enzyme, dye, and buffer combination are capable of detecting the presence of the marker for marijuana in the person's saliva, and, when such marker is detected, are capable of causing the drug-sensitive pad to change color.

As stated above, the drug-sensitive pad is sensitive to a particular, specific drug, such as marijuana. Often, though, a parent or employer will want to test their son, daughter, or employee for more than one drug, such as, marijuana, cocaine, opiates, PCP, amphetamines, methamphetamines, or barbituates. Thus, the personal drug testing kit of the present invention may include more than one drug-sensitive pad 12, with each pad being sensitive to a different, specific drug. For instance, a second drug-sensitive pad 20 may be included in the testing kit that is sensitive to another, specific drug, such as cocaine. The cocaine-sensitive pad 20 would therefore be saturated with the enzyme or enzymes that are sensitive to the marker for cocaine that will be present in a person's saliva when the person has ingested cocaine and the cocaine is still present in the person's bloodstream. In addition, this pad should further include one or more dyes and buffers which will cause a change in color when the cocaine-sensitive enzyme or enzymes are activated by the cocaine marker in the saliva. Again, any enzyme, dye, and buffer, or combination thereof, may be selected, so long as the enzyme, dye, and buffer combination are capable of detecting the presence of the marker for cocaine in the persons saliva, and when such marker is detected, are capable of causing the drug-sensitive pad to change color.

Similarly, drug-sensitive pads 12 for other drugs, such as opiates, PCP, amphetamines, methamphetamines, and barbituates, may also be included. These pads would also have an enzyme or enzymes that are sensitive to the particular drug and would have dyes and buffers that would cause a change in color when the particular drug marker is detected in the person's saliva. As with the marijuana and cocaine examples provided above, any enzyme, dye, and buffer, or combination thereof, may be selected, so long as the enzyme, dye, and buffer combination are capable of detecting the presence of the marker for any of these drugs in the person's saliva, and when such marker is detected, are capable of causing the drug-sensitive pad to change color.

The drug-sensitive pads 12 are preferably mounted by any adhesive well-known in the art to one end of a thin plastic stick 14. (See FIGS. 1 and 2). Any type of plastic that can be formed into thin flexible sticks that is well-known in the art may be used to form stick 14. The stick 14 is preferably as wide as the drug-sensitive pad 12 and long enough so that the user can place the drug-sensitive pad within his mouth without placing the user's hand into the user's mouth. Additionally, the stick may be formed from any other substantially rigid and inert material, such as wood or metal, if desired.

Because the testing kit may be used to simultaneously detect more than one drug, more than one drug-sensitive pad 12 may be mounted onto each stick. (FIG. 1). Each drug-sensitive pad 12 may be capable of detecting a different drug. Thus, with one application of saliva to one stick, the user may be able to test for more than one drug. If any of the pads 12 were to detect a drug and thus change color, the user would then have to determine from the packaging 16, as described below, which drug was detected.

Each drug-sensitive pad 12 is cut into small pieces and are rectangularly shaped, preferably being one quarter inch long by three-eighths inches wide. If desired, the pads 12 may be cut into any shape so long as the pad will fit onto the end portion of the stick 14 that can be easily inserted into the user's mouth and saturated with saliva. The end of the stick 14 that contains the pads may be wider than the remainder of the stick that does not contain the pads 12 to make it clear to the user which portion of the stick 14 should be saturated with the saliva.

The enzymes that are used on the pads 12 are sensitive to exposure to ultraviolet light, moisture, and air and will lose their activity if they are exposed to any of these elements for an appreciable amount of time. Thus, the package 16 of the present invention is particularly suited for storing the drug-sensitive pads 12 of the testing kit 10 without exposing them to ultraviolet light, moisture, or air. The package 16 preferably comprises a first side wall 22 and a second side wall 24. Both the first and second side walls (22 and 24, respectively) preferably comprise an inner and outer layer, (26 and 28, respectively, for the first side wall and 30 and 32, respectively, for the second side wall). The inner layer 26 of the first side wall 22 and the inner layer 30 of the second side wall 24 is preferably formed from aluminum foil.

The aluminum foil used is preferably a high grade surgical aluminum foil. It has been found that the high grade surgical aluminum foil is preferred over other types of aluminum foils because this type of aluminum foil does not give off any oils that could damage the drug-sensitive pads during prolonged storage times. Conventional aluminum foils that are typically used in packaging may give off the oils and residues that are imparted to the aluminum foil during manufacture when exposed to elevated temperatures, such as room temperature and the temperatures found when stored in a warehouse or on an automobile dashboard. For this reason, high grade surgical aluminum foil may be chosen instead. High grade surgical aluminum foil differs from conventional aluminum foil in that it is specially washed during manufacture to remove the impurities normally found in conventional aluminum foil. Thus, the term high grade surgical aluminum foil is used herein to describe aluminum foil that is in a condition wherein it is free from impurities such as oils and other foreign matter. The use of the high grade surgical aluminum foil therefore provides the distinct benefit of allowing the drug-sensitive pads 12 of the present invention to be stored within a package 16, without exposing the pads 12 to ultraviolet light, moisture, air, or any other impurities. Further, the packaging provides the additional benefit that the pads 12 do not have to be stored under refrigerated conditions, but, rather can be stored at room temperature, or even in a warehouse or on the dashboard of a car.

In the alternative, the inner layers 26, 30 of the first and second side walls 22 and 24 of the packaging 16 may comprise conventional aluminum foil which has been coated on at least one surface with a polymer. If the surface of the aluminum foil having the polymer is utilized as the inner layer of the side walls that contacts the drug-sensitive pads, then the polymer coating will prevent the oils of the conventional aluminum foil from coming into contact with the drug-sensitive pads that are located within the package. Any polymer and any means for coating the conventional aluminum foil known in the art may be used, so long as the foil/polymer combination are capable of providing a packaging which prevents the drug-sensitive pads from coming into contact with ultraviolet light, moisture, or air.

The outer layer 28 of the first side wall 22 and the outer layer 32 of the second side wall 24 are preferably formed from paper. By providing a first and second side wall, 22 and 24, that are formed from paper and aluminum, the first and second side walls of the package 28, 32, are easily opened by tearing by the user. Although paper is preferred as the outer layer of the first and second side walls, 22, 24, any material may be used that will provide a carrier for the aluminum foil that comprises the inner layer 26, 30 of the side walls 22, 24 and provide the benefit of preventing exposure of the drug-sensitive pads contained within the packaging to ultraviolet light, moisture, and any other impurities.

As shown in FIG. 2, the first side wall 22 is formed by coupling together the surface 34 of the layer 28 of the first side wall 22 with the surface 36 of the inner layer 26 of the first side wall 22. When coupled together, the outer edge 38 of the outer layer 28 is preferably contiguous with the outer edge 40 of the inner layer 26. Any type of adhesive material that is well-known in the art for coupling aluminum foil to paper may be used for coupling together these two layers. The second side wall 24 is formed by coupling together the surface 42 of the inner layer 30 of the second side wall 24 with the surface 44 of the outer layer 32 of the second side wall 24. When coupled together, the outer edge 46 of inner layer 30 is preferably contiguous with the outer edge 48 of the outer layer 32. Again, any adhesive well-known in the art may be used for coupling these layers together.

The package 16 for storing the drug-sensitive pads of the personal drug testing kit 10 of the present invention is then preferably formed by coupling together the outer edge 40 of the inner layer 26 of the first side wall 22 with the outer edge 46 of the inner layer 30 of the second side wall 24 to form an interior 18 for storing at least one drug-sensitive pad 12. (See FIG. 2). The inner layer 26 of the first side wall 22 and the inner layer 30 of the second side wall 24, which are both preferably formed from high grade surgical aluminum, are facing each other and form the inside lining of the interior 18 of the package 16.

When the first side wall 22 and the second side wall 24 are coupled together, the drug-sensitive pads 12, which are attached to sticks 14, are placed between the two side walls in a vacuum environment so that the drug-sensitive pads do not contact any air when they are placed into the package 16 or when they are stored in the interior 18 of the package 16. Thus, the drug-sensitive pads 12 of the testing kit 10 are maintained within an environment in which their only contact is with the inner layer 26 of the first side wall 22 and the inner layer 30 of the second side wall 24, both preferably formed from the high grade surgical aluminum foil. The exterior of the package 16 that is exposed to ultraviolet light, moisture and air, are the outer layer 28 of the first side wall 22 and the outer layer 30 of the second side wall 32, which are formed from paper. The package 16, having the high grade surgical aluminum foil interior (or polymer coated aluminum interior) and paper exterior is able to store the drug-sensitive pads 12 of the testing kit in its interior 18 without exposing the drug-sensitive pads 12 to any ultraviolet light, moisture or air.

The instructions for administering the drug test may also be printed on the exterior 50 of the package 16 along with the location of the particular pads, as described above. By printing the instructions and the location of the pads, a self-contained personal blood test is provided, that is, the entire test is contained within and on the packaging.

Figure 3:
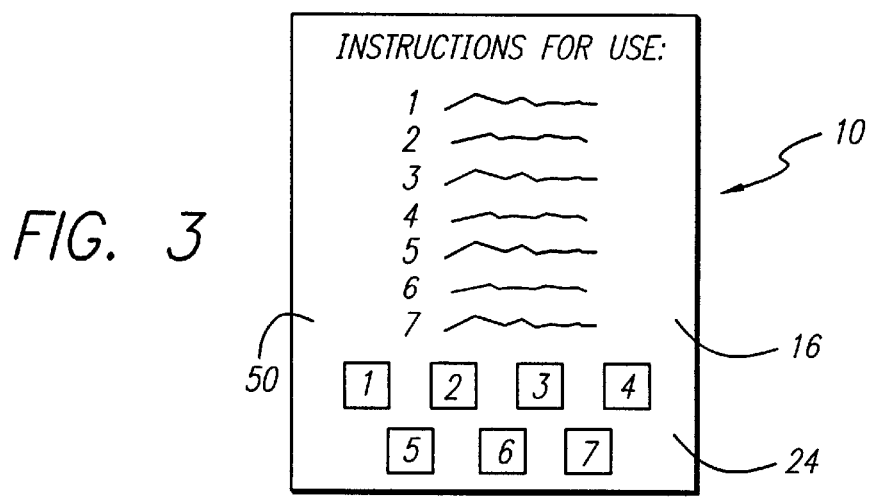
FIG. 3 is a top elevational view of the exterior of the package showing the instructions for use and color changes and their corresponding drugs printed thereon with which one embodiment of the present invention can be used.

The drug-sensitive pads 12 are designed to change color if the marker for the desired drug is detected in the user's saliva. Thus, if the drug marker is detected, the pad 12 will change color and the test will be positive for that drug. If no drug marker is detected, there will be no change in color and the test for that drug is negative. If more than one drug is being tested for by test kit, then the packaging 16 may indicate on the outer surface of the packaging the location of the particular pads 12 on the sticks 14 and the drugs for which they are intended to detect. Thus, for instance, if there are seven drugs being tested for by a particular test kit, there may be seven pads 12 located on the stick 14 in a certain order—from the farthest end—(1) marijuana, (2) cocaine, (3) opiates, (4) PCP, (5) amphetamines, (6) methamphetamines, and (7) barbituates. The exterior 50 of the packaging 16 may have printing that would show the location of these pads on the sticks and the drug for which they are each testing. (FIG. 3). Thus, after application of the saliva, if there is a color change, the user can very easily compare the color changes of the pad or pads 12 and compare it with the location of the pads 12 and the particular drug indicated on the exterior 50 of the packaging 16. The user would therefore be capable of easily and quickly determining the results of the test.

The user preferably performs the drug test as follows. First, the user should abstain from eating or drinking for at least 15 minutes prior to taking the test. The user then opens the package 16 by tearing open the first and second side walls, 22 and 24, respectively, to reveal the drug-sensitive pads 12 and sticks 14 within the interior 18. The user then preferably saturates the drug-sensitive pads 12 with the user's saliva, preferably by either placing the drug-sensitive pad end of the stick 14 into the mouth and saturating the drug-sensitive pad 12 with saliva. The user may also place their saliva in a cup and saturate the drug-sensitive pad 12 in the saliva. The user then preferably waits approximately two minutes for the drug-sensitive pad 12 to become activated and change color, if the presence of the drug being tested is detected. The user then compares the color changes of the drug-sensitive pads 12, if any, with the location of the pads that is printed on the exterior 50 of the package 16. If no color change is detected, then the test is negative for all drugs tested. If one or more pads 12 change color, then the drugs being detected by those pads 12 were detected and they are thus present in the system of the person being tested. Thus, as can be seen, the test is easy to administer and does not require the taking of blood or urine by the user. Further, it can be seen that the test is self-contained and requires no other outside parts other than the user's saliva to perform.

In a further preferred embodiment of the present invention, the first and second side walls 22 and 24 respectively, are rectangularly shaped. It is preferable that the package containing the personal drug testing kit be portable so that it can be discreetly carried in a wallet, pocket or purse. Thus, one size for making the first and second side walls 22, 24 is a size approximating that of a business card, which are commonly held within a wallet. This size is preferably rectangular, being three and a half inches long by two inches wide.

In another embodiment of the present invention, the first side wall 22 further comprises a plastic covering layer 52 coupled together with the upper surface 54 of the outer layer 28 of the first side wall 22. (See FIG. 2). The plastic covering layer 52 may also be coupled to the lower surface 56 of the outer layer 32 of the second side wall 24 (Not shown in FIG. 2). The plastic covering layer 52 is substantially rigid to protect the drug-sensitive pads 12 and sticks 14 contained within the package 16 from any bending that may occur while the package is stored within a wallet, pocket or purse of the user. The plastic covering layer is preferably formed from any plastic that can be formed into thin, substantially rigid sheets that can be imprinted with color printing.

While a particular form of the invention has been illustrated and described, it will be apparent that various modifications can be made without departing from the scope of the invention. For instance, the size and shape of the first and second side walls 22, 24 may be chosen as preferred by the manufacturer in any size and shape so long as the sticks 14 and the drug-sensitive pads 12 are contained within the interior of the package. Accordingly, it is not intended that the invention be limited by the specific embodiment disclosed in the drawings and described in detail hereinabove.

I claim:

1. A personal drug testing kit for testing the presence of at least one predetermined drug in the system of a user, comprising:

at least one pad being chemically sensitive to the predetermined drug; and a package, the pads being stored within the package;
wherein the predetermined drug is selected from the group comprising: marijuana, cocaine, opiates, PCP, amphetamines, methamphetamines, and barbiturates.

2. The personal drug testing kit of claim 1 further including at least one stick having and end wherein the pad is attached to the end of the stick and wherein the stick is stored within the package.

3. The personal drug testing kit of claim 1 wherein the pad is formed from paper and is impregnated with at least one enzyme that is sensitive to the predetermined drug, at least one dye and at least one buffer, wherein when the drug sensitive enzyme comes in contact with the user's saliva, the dye changes color only if the predetermined drug is present in the system of the user.

4. The personal drug testing kit of claim 1 wherein the package has an exterior having the instructions for use of the personal drug testing kit printed thereon.

5. The personal drug testing kit of claim 1, wherein the package has an exterior surface and an interior surface and wherein the interior surface comprises aluminum foil.

6. The personal drug testing kit of claim 5, wherein the aluminum foil is high-grade surgical aluminum foil.

7. The personal drug testing kit of claim 5, wherein the aluminum foil is coated with a polymer.

8. A personal drug testing kit for testing the presence of at least one predetermined drug in the system of a user, comprising:

at least one pad being chemically sensitive to the predetermined drug; and a package having an interior being formed from high grade surgical aluminum foil, the pads being stored within the package;
wherein the predetermined drug is selected from the group comprising: marijuana, cocaine, opiates, PCP, amphetamines, methamphetamines, and barbiturates.

9. The personal drug testing kit of claim 8 further including at least one stick having an end wherein the pad is attached to the end of the stick and wherein the stick is stored within the package.

10. The personal drug testing kit of claim 8 wherein the exterior of the package comprises paper.

11. The personal drug testing kit of claim 8 wherein the pad is formed from paper and is impregnated with at least one enzyme that is sensitive to the predetermined drug, at least one dye and at least one buffer, wherein when the drug sensitive enzyme comes in contact with the user's saliva, the dye changes color only if the predetermined drug is present in the system of the user.

12. The personal drug testing kit of claim 8 wherein the package has an exterior having the instructions for use of the personal drug testing kit printed thereon.

13. The personal drug testing kit of claim 8 wherein the package has an enclosed interior, the enclosed interior containing substantially no air.

14. A personal drug testing kit for testing the presence of at least one predetermined drug in the system of a user, comprising:

at least one pad being chemically sensitive to the predetermined drug; and a package, the pads being stored within the package;
wherein the package has an exterior surface and an interior surface, the interior surface comprises aluminum foil, the aluminum foil is coated with a polymer, and wherein the predetermined drug is selected from the group comprising: marijuana, cocaine, opiates, PCP, amphetamines, methamphetamines, and barbiturates.

15. A personal drug testing kit for testing the presence of at least one predetermined drug in the system of a user, comprising:
   at least one pad being chemically sensitive to the predetermined drug, the pad being formed from paper and being impregnated with at least one drug-sensitive enzyme, at least one dye and at least one buffer, wherein the drug-sensitive enzyme comes in contact with the user's saliva, the dye changes color; and
   a package for storing the pad, the package being formed from paper and high grade surgical aluminum foil;
   wherein the predetermined drug is selected from the group comprising: marijuana, cocaine, opiates, PCP, amphetamines, methamphetamines, and barbiturates.

16. The personal drug testing kit of claim 15 wherein the package includes:
   a first side wall having an outer edge and being comprised of a plurality of layers coupled together, at least one of the layers being formed from aluminum foil; and
   a second side wall having an outer edge and being comprised of a plurality of layers coupled together, at least one layer being formed from aluminum foil,
   wherein the outer edge of the first side wall is coupled together with the outer edge of the second side wall to form an interior for storing at least one drug-sensitive pad.

17. The personal drug testing kit of claim 14 further including at least one stick having an end wherein the drug-sensitive pad is attached to the end of the stick and wherein the stick is stored within the interior of the package.

18. The personal drug testing kit of claim 16 wherein one of the layers of the first side wall is a substantially rigid plastic layer.

19. The personal drug testing kit of claim 16 wherein one of the layers of the first side wall is printed with the instructions for use of the drug testing kit.

20. The personal drug testing kit of claim 16 wherein at least one of the layers of the first side wall and at least one of the layers of the second side wall are formed from paper.

21. The personal drug testing kit of claim 16 wherein the aluminum foil layer of the first side wall and the aluminum foil layer of the second side wall comprises a high grade surgical aluminum foil.

22. The personal drug testing kit of claim 16 wherein the aluminum foil layer of the first side wall and the aluminum foil layer of the second side wall is coated with a polymer.

23. The personal drug testing kit of claim 15 wherein the interior of the package contains substantially no air.

24. A method for determining the presence of at least one predetermined drug in the system of a user, comprising:
   opening a package comprising aluminum foil and containing at least one pad being chemically sensitive to a predetermined drug;
   saturating one of the pads with the user's saliva; and
   waiting approximately two minutes to determine whether the pad has detected the presence of the drug by changing its color;
   wherein the predetermined drug is selected from the group comprising: marijuana, cocaine, opiates, PCP, amphetamines, methamphetamines, and barbiturates.

25. The method of claim 24 wherein the package comprises a high grade surgical aluminum foil.

26. The method of claim 24 wherein the aluminum foil of the package is coated with a polymer.

27. A kit as defined in claim 1, wherein said group constitutes marijuana, cocaine, opiates, PCP, amphetamines, methamphetamines, and barbiturates.

28. A kit as defined in claim 8, wherein'said group constitutes marijuana, cocaine, opiates, PCP, amphetamines, methamphetamines, and barbiturates.

29. A kit as defined in claim 14, wherein said group constitutes marijuana, cocaine, opiates, PCP, amphetamines, methamphetamines, and barbiturates.

30. A kit as defined in claim 15, wherein said group constitutes marijuana, cocaine, opiates, PCP, amphetamines, methamphetamines, and barbiturates.

31. A kit as defined in claim 24, wherein said group constitutes marijuana, cocaine, opiates, PCP, amphetamines, methamphetamines, and barbiturates.

* * * * *